(12) United States Patent
Bonnevay et al.

(10) Patent No.: US 12,205,413 B2
(45) Date of Patent: Jan. 21, 2025

(54) METHOD FOR ACQUIRING DATA CAPTURED BY A CAPTURE MODULE EMBEDDED IN A MOBILE DEVICE FOLLOWING A PREDETERMINED TRAJECTORY, CORRESPONDING COMPUTER PROGRAM AND DEVICE

(71) Applicant: ALSTOM Transport Technologies, Saint-Ouen-sur-Seine (FR)

(72) Inventors: Vincent Bonnevay, Lyons (FR); Hubert Andre, Villeurbanne (FR)

(73) Assignee: ALSTOM Transport Technologies, Saint-Ouen-sur-Seine (FR)

( * ) Notice: Subject to any disclaimer, the term of this patent is extended or adjusted under 35 U.S.C. 154(b) by 266 days.

(21) Appl. No.: 16/828,596

(22) Filed: Mar. 24, 2020

(65) Prior Publication Data
US 2020/0312052 A1  Oct. 1, 2020

(30) Foreign Application Priority Data
Mar. 25, 2019  (FR) ...................................... 1903097

(51) Int. Cl.
*G07C 5/00* (2006.01)
*G01N 33/00* (2006.01)
(Continued)

(52) U.S. Cl.
CPC ......... *G07C 5/008* (2013.01); *G01N 33/0062* (2013.01); *G05B 19/4183* (2013.01);
(Continued)

(58) Field of Classification Search
CPC ... G06F 16/9035; G07C 5/0808; G07C 5/085; G07C 5/008; H04N 5/23212; G05B 19/4183; G01N 33/0062
See application file for complete search history.

(56) References Cited

U.S. PATENT DOCUMENTS 9,663,128 B2 *  5/2017  Johnson ................ B61L 25/026
9,843,893 B2 * 12/2017  Haro ..................... H04W 4/021
(Continued)

FOREIGN PATENT DOCUMENTS

EP      2881710 A1     6/2015
JP   2019218022 A  * 12/2019

OTHER PUBLICATIONS

Bogdan Tomoyuki Nassu, Masato Ukai; Rail Extraction for Driver Support in Railways, Jun. 5, 2011, IEEE Intelligent Vehicles Symposium, p. 83-88 (Year: 2011).*

(Continued)

*Primary Examiner* — Khoi H Tran
*Assistant Examiner* — Dairon Estevez
(74) *Attorney, Agent, or Firm* — Soquel Group LLC

(57) ABSTRACT

A method for acquiring data, in an electronic acquisition module, detected by a sensor embedded on a vehicle with a predefined trajectory, including the following operations implemented in real time by an electronic acquisition module including a database defining, for each of a plurality of points of the predefined trajectory, a set of subsections of interest indicating at least one subsection of interest in the acquisition zone of the sensor: determining a next position of the moving vehicle on the predefined trajectory of the moving vehicle, and determining, as a function of at least the subsection of interest defined by the database for the point corresponding to the determined position, the value of a parameter included among acquisition of the data by the embedded sensor in the next position, or a processing parameter of the data captured by the embedded sensor in the next position.

9 Claims, 3 Drawing Sheets

(51) Int. Cl.
*G05B 19/418* (2006.01)
*G07C 5/08* (2006.01)
*H04N 23/67* (2023.01)

(52) U.S. Cl.
CPC ............ *G07C 5/0808* (2013.01); *G07C 5/085* (2013.01); *H04N 23/67* (2023.01)

(56) References Cited

U.S. PATENT DOCUMENTS

| | | | |
|---|---|---|---|
| 10,017,115 B2* | 7/2018 | Lavoie | B62D 15/027 |
| 10,481,600 B2* | 11/2019 | Yen | G05D 1/0027 |
| 11,067,995 B2* | 7/2021 | Weiser | G06N 3/02 |
| 2006/0098843 A1* | 5/2006 | Chew | B61L 23/041 |
| | | | 382/104 |
| 2007/0058048 A1* | 3/2007 | Kinugasa | B60R 1/00 |
| | | | 348/E5.034 |
| 2010/0104199 A1* | 4/2010 | Zhang | G08G 1/166 |
| | | | 382/199 |
| 2015/0008294 A1* | 1/2015 | Desbordes | G06T 7/20 |
| | | | 246/122 R |
| 2018/0054559 A1 | 2/2018 | Welker | |
| 2019/0180118 A1* | 6/2019 | Kraeling | G01S 11/12 |
| 2019/0236955 A1* | 8/2019 | Hu | G05D 1/0212 |
| 2020/0101989 A1* | 4/2020 | Dick | G01N 25/72 |

OTHER PUBLICATIONS

INPI Rapport de Recherche Preliminaire for Patent Application No. FR 1903097, Nov. 21, 2019, 2 pp.

* cited by examiner

METHOD FOR ACQUIRING DATA CAPTURED BY A CAPTURE MODULE EMBEDDED IN A MOBILE DEVICE FOLLOWING A PREDETERMINED TRAJECTORY, CORRESPONDING COMPUTER PROGRAM AND DEVICE

CROSS-REFERENCE TO RELATED APPLICATIONS

This application claims priority of French Patent Application No. 19 03097, filed on Mar. 25, 2019.

FIELD OF THE INVENTION

The present invention relates to the field of moving vehicles, for example a train, embedding a sensor, for example, an image sensor (camera), a radar sensor or a LIDAR sensor, capable of detecting data relative to the environment of the train. Such trains generally include a member for processing detected data configured to perform processing inter alia on the detected data and on the obstacle detection type, in order to trigger, for example automatically, a slowing or emergency stop, or such other action.

The present invention more specifically relates to a data acquisition method, via an electronic acquisition module, data being detected by one or several data capture modules including at least one sensor embedded on a moving vehicle and delivering, at each acquisition moment of the sensor, a set of data corresponding to the acquisition zone of the sensor, according to which the moving vehicle follows a predefined trajectory.

BACKGROUND OF THE INVENTION

A large quantity of data thus captured proves difficult to use due to contradictory data, exposure or exploitation problems of the sensors, in particular regarding the images taken just before entering a tunnel, which generally show nothing of the trajectory, which are found in a black halo corresponding to the tunnel; or exploitation difficulties for data captured by a LIDAR sensor inter alia in a misty or dusty environment or during precipitation.

Furthermore, there is a need to still further decrease the time and computing resources necessary to process such images.

SUMMARY OF THE DESCRIPTION

The aim of the invention is to propose a method that makes it possible to improve the situation. To that end, according to a first aspect, the invention proposes a method of the aforementioned type, characterized in that the electronic acquisition module includes a database defining, for each of a plurality of points of the predefined trajectory, a set of subsections of interest indicating at least one subsection of interest in the acquisition zone of the sensor, the method including the following operations implemented in real time by the acquisition module:
determining a next position of the moving vehicle on the predefined trajectory of the moving vehicle;
determining, as a function of at least the subsection of interest defined by the database for the point corresponding to the determined position, the value of at least one parameter included among image capture parameters of the data by the embedded sensor in the next position, and processing parameters of the data captured by the embedded sensor in the next position.

The invention thus makes it possible to limit the analysis/acquisition of the captured data (images), to a reduced portion (that of interest) in order to decrease the processing time and/or resources and to optimize the values of the capture parameters of the acquisition module(s) in light of what it will be useful to exploit.

In embodiments, the method according to the invention further includes one or more of the following features:
the sensor is an image sensor suitable for capturing images as a function of determined values of image capture parameters of the sensor, according to which the image capture parameter is a parameter among the focal distance, the focal area, the contrast, the white balance, orientation of the image sensor, scanning zone, range, frequency or frequencies used, and estimated size of the objects sought;
determination of the current values of parameters is performed as a function of the subsection of interest and to the exclusion of subsections not indicated in the subsection of interest;
a subsection of interest is in the set including an upcoming trajectory portion and an element to be excluded;
a subsection of interest corresponds to an end of a tunnel;
determination of the values of parameters is further done as a function of meteorological data;
the following steps are carried out by the acquisition module;
identification of an exploitation problem, or incompleteness, of data coming from the sensor; and
following identification, triggering supply of complementary data by a data acquisition system not embedded in the moving vehicle.

According to a second aspect, the present invention proposes a computer program including software instructions which, when executed by a computer, carry out a method as defined above.

According to a third aspect, the present invention proposes an electronic module for acquiring data detected by a data capture module including at least one sensor delivering, at each acquisition instant of the sensor, a set of data corresponding to the acquisitions of the sensor and embedded in a moving vehicle following a predefined trajectory, the electronic acquisition module being characterized in that it includes a database defining, for each of a plurality of points of the predefined trajectory, a set of subsections of interest indicating at least one subsection of interest in the acquisition zone of the sensor, and in that it is suitable for determining, in real time, a next position of the moving vehicle on the predefined trajectory of the moving vehicle, for determining, as a function of at least the subsection of interest defined by the database for the point corresponding to the determined position, the value of at least one parameter included among the image capture parameters of the data by the embedded sensor in the next position and processing parameters of the data detected by the embedded sensor in the next position, and for commanding the operation among the detection and the processing according to the value of the parameter.

According to a fourth aspect, the present invention proposes a vehicle suitable for following a predefined trajectory, including the electronic data acquisition module according to the invention and including the embedded sensor delivering, at each acquisition instant of the sensor, a set of data corresponding to the acquisition zone of the sensor.

BRIEF DESCRIPTION OF THE DRAWING

These features and advantages of the invention will appear upon reading the following description, provided solely as an example, and done in reference to the appended drawings, in which.

DETAILED DESCRIPTION

Figure 1:
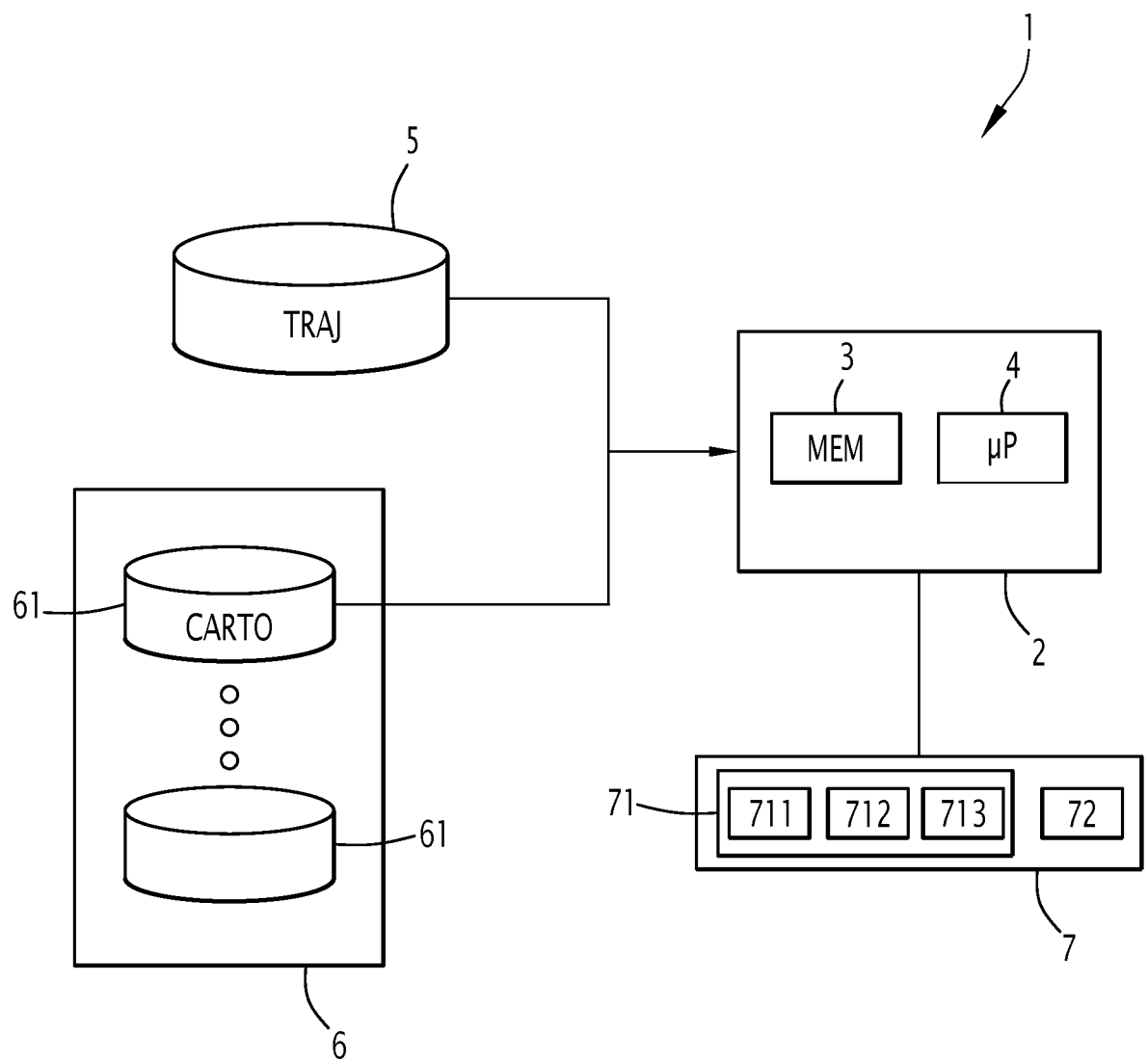
FIG. 1 shows a view of an image acquisition system in one embodiment of the invention.

FIG. 1 shows a system 1 for acquiring data measured/detected by observation sensors of the environment of a vehicle.

In the considered embodiment, acquisition system 1 is suitable for optimizing the obtainment and/or exploitation of data captured from data detection sensors, such as one or several cameras, and/or one or several LIDAR(s) (Laser Detection and Ranging) and/or one or several radar(s) embedded in a train (not shown). Acquisition system 1 makes it possible to make the captured data, in particular the captured images, more usable and/or to decrease the time or the computing resources necessary to exploit the detected data, in particular the images.

The train is, for example, controlled by an autonomous automatic driving device, or by a driver optionally assisted by such an automatic driving device.

The train follows a predetermined trajectory and speed between a starting point and an arrival point, optionally including intermediate stopping points, on rails.

In the description, the described vehicle is a train, but this vehicle is more generally able to be any type of vehicle, particularly a guided vehicle, in particular a rail vehicle.

Acquisition system 1 includes a control block 2, a trajectory memory 5, hereinafter designated memory TRAJ 5, a set 6 of information sources and a data delivery module 7.

Memory TRAJ 5 includes data for defining the trajectory of the train between its departure point and its arrival point, therefore corresponding to the outline of the rails, in the form, for example, of geographical coordinates (e.g., in the form longitude, latitude, altitude) of points producing a sampling of the trajectory.

Figure 3:
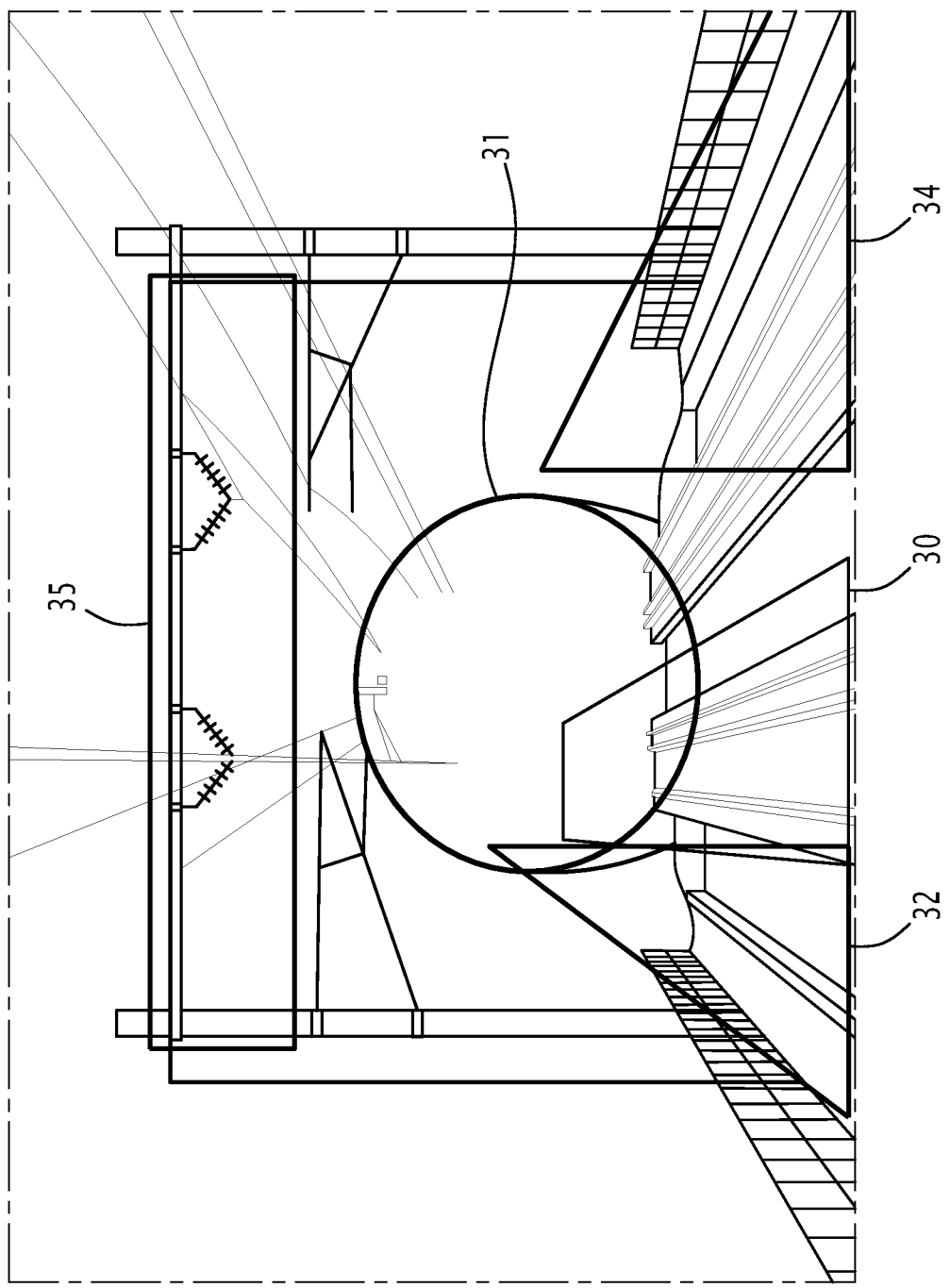
FIG. 3 is a view illustrating a division into subsections of one embodiment of the invention.

FIG. 3 illustrates an image taken from a data sensor, in particular a camera 711, i.e., from a point of the trajectory of the train. FIG. 3 shows a railroad track on the left corresponding to the trajectory followed from the capture point of the image, by the train, and the entrance to a tunnel, through which the railroad track passes.

Set 6 of information sources includes one or several databases 61, including a database hereinafter referred to as CARTO 61.

Database CARTO 61 includes, for each of the trajectory points stored in memory TRAJ 5 (or for each of a subset of trajectory points stored in memory TRAJ 5), the definition of one or several subsections of an image of the trajectory captured in the considered point (in one embodiment, the union of the subsections being strictly less than the entirety of the image).

For each of the subsections associated with a trajectory point, there is further associated at least one respective information item, relative to the image detection at this trajectory point or with the processing of the captured images at this point, as well as, optionally, outside data (inter alia meteorological data, railway traffic data, a danger signal on the track).

For example, a subsection delimits the trajectory portion to be followed by the train (i.e., in the case of the train, the railroad track portion) and appearing in the image, or at least the portion of this trajectory closest to the train, and thus isolates it from the rest of the image: such a subsection corresponds to subsection 30 in the image shown in FIG. 3.

For example, a subsection delimits the entrance to or exit from a tunnel through which the trajectory passes: such a subsection corresponds to subsection 31 in the image shown in FIG. 3.

For example, a subsection delimits a zone within which a danger may occur (presence of objects or individuals that may require slowing of the train, or even emergency braking), for example, delimiting the immediate vicinity of the trajectory at the considered point: such a subsection, for example, corresponds to subsection 32 or subsection 34 in the image shown in FIG. 3.

For example, subsection 35 of FIG. 3, corresponding to the upper part of the end of the tunnel under which the train will imminently pass, is a danger zone known for its risk of rockslides; this is also a zone of the image, depending on the passage time of the train, which may be exposed to a sunset, subject to glare causing saturation of camera sensor 711. Control block 2 is suitable for determining parameter values, as described hereinbelow, and for commanding implementation of the determined values at the data delivery module, in particular for images.

Data delivery module 7 includes a set 71 of sensor(s) including at least one sensor and a captured data processing block 72.

In the considered case, set 71 of sensor(s) includes three data sensors, in particular for images, (a camera 711, a LIDAR 712, a radar 713). Data delivery module 7 is a data delivery module for images captured by the image sensors, and data processing block 72 is a data processing block for captured images.

The image sensors (e.g., in the example considered here, camera 711, is of the LCD or other type, LIDAR image sensor 712 is a sensor based on the echo of laser beams, radar sensor 713 is a sensor based on the echo of radio waves) are suitable for capturing, at each acquisition instant Tn (for example every MS milliseconds, with MS included in a range of values from 100 to 1500, adjustable as a function of the movement speed of the train and/or outside environmental parameters, or in a plurality of predetermined geographical positions, e.g., corresponding to the geographical positions stored in database CARTO 61), an image of the geographical zone corresponding to the acquisition zone of the sensor and to deliver the captured image to image processing block 72.

Camera 711 includes means for adjusting values of image capture parameters. These image capture parameters, for example, include: the focal distance and/or the focal area and/or the contrast and/or the white balance and/or the processing filters of the camera.

LIDAR 712 and radar 713 include means for adjusting values of image capture parameters. These image capture parameters include, for example: a type of scanning, targeted zones, frequencies used, and a range.

Camera 711, LIDAR 712 and radar 713 are, in the considered example, attached to the front of the train and therefore capture images of a zone of the environment facing the train in its running direction. Certain other elements of image acquisition system 1, according to the embodiments, may or may not also be embedded. The data exchanges between the various elements of acquisition system 1 take place by means of telecommunications links between these elements, wired or wireless, in particular radiofrequency.

Processing block 72 is suitable for performing processing on the images delivered by sensors 711, 712, 713, as a function of values of parameters defining the performed processing. These processing operations include, for example, over the entire image, or selectively over subsections of the image: detecting the presence of objects, identifying the type of objects detected, and evaluating the distance to a detected object. The parameters, for example, define which subsection is affected by the processing to be applied, or which subsections are affected, which respective processing operation(s) are to be performed on each of these subsections (separate processing operations may be applied on separate sub-portions of an image).

In the considered embodiment, control block 2 includes a memory 3 and a microprocessor 4. Memory 3 stores software instructions which, during their execution by microprocessor 4, implement the method described below with reference to FIG. 2 and fall to control block 2.

In another embodiment, control block 2 is made in the form of a programmable logic component, such as an FPGA (Field Programmable Gate Array), or in the form of a dedicated integrated circuit, such as an ASIC (Application Specific Integrated Circuit).

Figure 2:
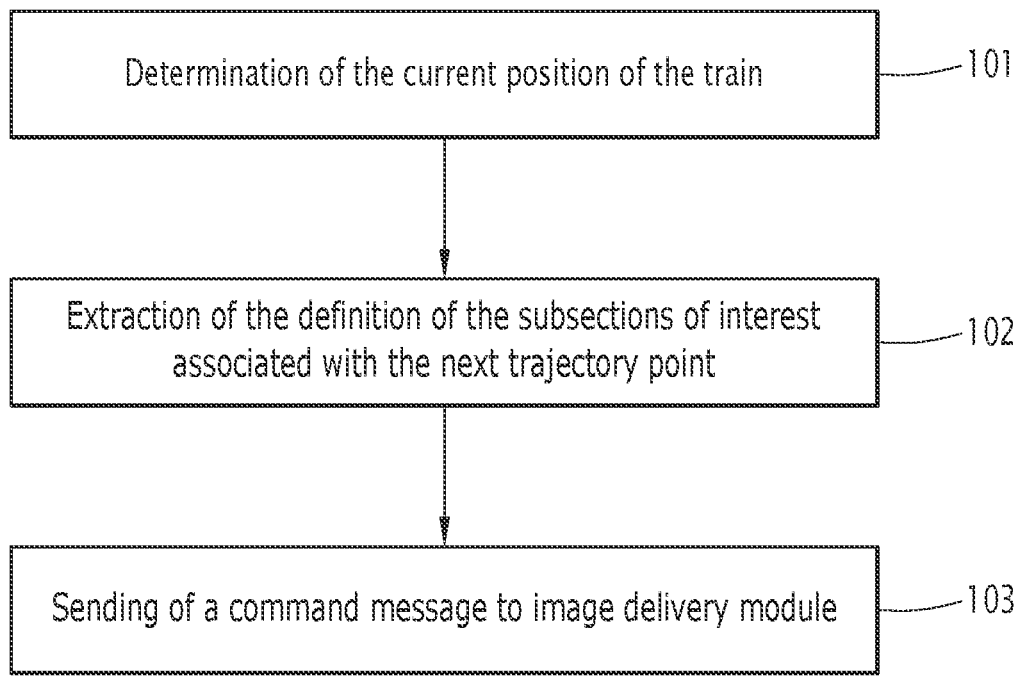
FIG. 2 is a flowchart of steps implemented in one embodiment of the invention.

FIG. 2 shows a flowchart of operations carried out in one embodiment of the invention.

At operation 101, control block 2 determines the current position of the train (for example, that of the point at which camera 711, LIDAR 712 and radar 713 installed on the train are located at that instant), designated as point P1 below.

This position may be determined in different ways: by a GPS sensor positioned on the train and/or by image processing by processing block 72, and/or by control block 2 as a function of the predetermined trajectory indicated in database CARTO 61 and instantaneous speeds of the train.

As a function of the current position P1 thus determined, memory TRAJ 5 and database CARTO 61, control block 2 determines what the next trajectory point P2 is that is present in database CARTO 61 by which the train will pass.

At operation 102, control block 2 extracts, from database CARTO 61, the definition of the subsections of interest associated with the next trajectory point P2, as well as the information associated with these subsections of interest appearing in database CARTO 61.

For each of these subsections, control block 2 determines, from the information associated with the subsection, a value of at least one image detection parameter for at least one of sensors 711, 712, 713 at the next trajectory point P2 and/or a processing parameter value by processing block 72 of the captured image at trajectory point P2 by at least one of these sensors.

At operation 103, control block 2 sends a command message to image delivery module 7 indicating at least the image detection parameter value for at least one of sensors 711, 712, 713 at the next trajectory point P2 and/or the processing parameter value. Image delivery module 7 next provides them to that or those of the affected sensors 711, 712, 713 (if it involves an image sensor parameter value) or the processing block 72 (if it involves an image processing parameter value).

During the passage to the next trajectory point P2, image sensors 711, 712, 713 then detect an image such that the value of each parameter having been subject to a command for this trajectory point P2 by control block 2 is set to the commanded value.

Each image captured at trajectory point P2 is next supplied to processing block 72, which processes it as a function of processing parameter values such that the value of each parameter having been subject to a command for trajectory point P2 by control block 2 is set to the value commanded by the latter relative to point P2.

These operations are performed in real time.

The applications are varied.

The images thus processed are next used to trigger certain actions: assistance for speed regulating systems (inter alia acceleration, deceleration), emergency stopping, and transmission of alerts to remote recipients for intervention (inter alia operational center, fire services, police).

According to the embodiments, only the subsections indicated in database CARTO 61, or only those of the specific image subsections corresponding to a certain type of information, benefit from processing (e.g., obstacle detection) by processing block 72, for example, zones 30, 31, 32, 34, 35), the rest of the image not being processed (or with a significantly lower priority).

For example, in most of the points of the trajectory, only the trajectory subsection will benefit from combined processing from the camera for immediate frontal obstacle detection on the track, the radar for long-range obstacle detection, and the LIDAR for medium-range lateral obstacle detection; whereas, once there is an approach to an entrance of the tunnel, aside from the trajectory subsection, the subsections corresponding to the sides of the track are also covered in processing the image from the camera. The upper part of the tunnel, the image from which will be strongly saturated by the sun, is excluded from the processing of the image from the camera and the subsection is processed primarily by appropriate scanning from the LIDAR or radar as a function of distance from the risk. This arrangement makes it possible to reduce processing times and/or computing resources necessary for processing, to best use the data/image capture systems embedded, in particular by adapting them to the contextual data, and to give priority to processing useful subsections.

In embodiments, the processing operations may be different on different subsections, and control block 2 determines the processing to be done on each sub-portion as a function of the information that is associated with the subsection in database CARTO 61: for example, upon arrival in a train station, near a platform, the subsections (or so-called zones) of interest will be the right or left platform (depending on the position of the railroad track) where the passengers are positioned and the areas where an object or person falls on the track. The LIDAR is primarily used to identify a falling movement (on the sub-portion corresponding to the platform edge), the camera is used to identify and recognize an object on the track (on the track subsection) and in the gauge of the passage of the train (this strategy can evolve as a function of outside weather information, e.g., exposure by head-on sunshine), the possibility of recovering images from cameras attached to the platform (or trains that are adjacent or arriving nearby) in order to process zones of interest that are complex and difficult to analyze from the train.

In another example, during approach of the train to a level crossing, subsections of interest are the lateral portions of the route crossing the railroad track. Maximum priority is put into place to detect an object present or crossing the route that could collide with the train. The distance between the route and the train being perfectly known (CARTO 61), the range configuration as well as the radar and LIDAR scanning angle are configured to best cover the affected subsections. The subsection of interest of camera 711 will primarily be over the detection of an immediate object or person on the track. Processing unit 72 verifies the possibility of an alert at the operational exploitation center, so as to determine whether an additional danger zone must be considered in the analysis. This strategy may be adapted as a function of outside weather information (head-on sun exposure), the possibility of recovering from cameras attached on the level crossing (or trains that are adjacent or arriving nearby) in order to process zones of interest that are complex and difficult to analyze from the train.

In embodiments, control block 2 determines, as a function of the associated information in database CARTO 61 and/or outside data (inter alia meteorological data, rail traffic data, danger signaling on the track), the contrast (and/or saturation), radar scanning, LIDAR values (and/or ranges) set for the different subsections of interest to be processed at point P2 corresponding, for example, to the image of FIG. 3 for each acquisition system, i.e., camera 711, LIDAR 712 and radar 713. Such an arrangement results in the trajectory area in the tunnel being usable for processing by processing block 72, whereas if the contrast value had been decided from the entire acquisition zone, the trajectory portion located in the tunnel would appear black in the black corresponding to the tunnel and would be unusable for image processing. This arrangement also makes it possible to most accurately adjust the radar and LIDAR scanning angle to correctly probe the inside of the tunnel (long range) and the upper part and sides of the tunnel (short ranges), thus improving the resolution of the images over the measuring times allotted to the acquisition. This arrangement in particular makes it possible to make the images fully exploitable both at the edge of the entrance to a tunnel and the edge of the exit from a tunnel.

In one embodiment, other complementary data are used as a function of the position: thus, outside data sources supply databases 61 other than database CARTO 61 of set 6 of databases, which then, for example, includes inter alia a meteorological database, a database relative to pollution, and a database relative to traffic. Data complementary to the train, such as the speed of the train, load of the train may further be used. In one embodiment of the invention, at operation 102, control block 2 extracts, from database CARTO 61, the definition of complementary weather, pollution, traffic, data associated with the next trajectory point P2 and speed, and control block 2 further determines the value of image capture parameters and/or the value of image processing parameters as a function of these complementary data relative to point P2. For example, while the train is still traveling in a tunnel and is approaching the exit from the tunnel, control block 2 determines the weather that will be present at the exit from the tunnel and decides on the filter to be applied by the camera as a function of the weather.

In one embodiment, a subsection of the image can be defined as a subsection to be excluded from processing by processing block 72 or to be excluded from the definition zone of the value of a capture parameter (e.g., corresponding inter alia to the location of shiny objects, reflective surfaces), dynamically or statically. For example, at operation 102, control block 2 determines, as a function of complementary data, that at the exit from the tunnel, during the image capture at the point P2, the sun will be facing the camera and present in the image. It is then suitable for delimiting a sub-portion of the image taken at point P2 including the sun, in order to command the camera to exclude this sub-portion from the acquisition zone from which camera 711 determines the value of the capture parameters and/or to command processing block 72 to exclude this sub-portion from the processing. A complementary analysis by radar or LIDAR or another alternative acquisition system (which would not be altered by the brightness of the disrupting object) may be commanded by processing block 72 if the excluded zone is part of a sub-portion of interest. This complementary analysis may also be commanded to an external acquisition system, if it is accessible by telecommunication, for example a track camera located nearby covering the sub-portion of interest.

In one embodiment, for a level crossing, there is fog, and control block 2 determines that the front camera (or the LIDAR or radar) cannot be used to verify that there is no car on the tracks 150 m ahead; it then connects, by telecommunication, to the fixed camera of the level crossing in order to recover the image and perform obstacle detection processing.

Or moreover, in one embodiment, control block 2 requests the reception, by wireless telecommunication, of data detected by a track sensor at the exit from the tunnel, in order to process the dangers at the tunnel exit that are inaccessible as long as the train is in the tunnel.

The present invention thus makes it possible, depending on the embodiments, to dynamically focus the image analysis force on reduced portions of each acquisition (those of interest) in order to decrease processing time and/or resources. For example, in the case of a subway, between two subway stations, only the trajectory sub-portion will be processed, while during the arrival at the station, the sub-portions corresponding to the platforms are also part of the processed zones.

Depending on the embodiment, the present invention allows the dynamic focusing of the determination of capture, scanning, range parameter values of the images (camera, LIDAR, radar), on reduced portions (those of interest) of the acquisition zone of the sensors in order to optimize these values of the capture parameters in light of what it will be useful to process.

These effects are particularly useful when the trains, or more generally the moving vehicles implementing the invention, include an autonomous guide module using the images or more generally the data, captured by a set of embedded sensor(s).

Thus, in the considered embodiment, the invention proposes a real-time interaction between the image processing and the guiding algorithm of the train in order to determine a specific zone of the image to be optimized (even if this damages the overall output of the rest of the image).

In embodiments, the acquisition zone of the sensor is a zone of the environment of the train facing the running of the train, as indicated above, or another zone near the train.

The example described above refers to the case of a train. Of course, the subject invention is applicable to the case of any vehicle whose trajectory is predefined (at least over a minimum duration of 5 seconds, this duration can be reduced as a function of the speed of the computing units and telecommunications systems in obtaining the data necessary for the methodology described above allowing the identification and processing of the zones of interest) and whose current position on the trajectory is known: subways, trams, buses and cars with autonomous driving or with a driving assistance module.

The invention claimed is:

1. An electronic module comprising:
a storage storing, for each of one or more sensors embedded in a rail vehicle, each sensor acquiring data in a respective acquisition zone and one of the sensors capturing images, and for each of a plurality of positions of the rail vehicle, respective first and second subsections of interest in the respective acquisition zone of the sensor, the union of the subsections of interest being strictly smaller than the acquisition zone;
a position processor determining, in real time, a next position of the rail vehicle, the next position being one of the plurality of positions;
a parameter controller setting in advance, for the next position, either
(i) one or more sensor values of a sensor image capture parameter values wherein at least one image the sensor capture parameter is a focal distance, a focal area, a contrast, a white balance, an orientation, a scanning zone, a range, a frequency or frequencies used, or an estimated size of an object sought in a captured image, the sensor image capture parameter values for the first and second subsections of interest being different, and
(ii) one or more values of a processing parameter values defining one or more processing operations to be performed on images captured by the sensors, the processing operations comprising, over an entire image or selectively over subsections of an image: detecting presence of objects, identifying types of objects detected, or evaluating distance to a detected object, the processing parameters defining which subsection(s) of an image is/are affected by a processing operation to be applied, or which respective processing operation(s) to apply on each of the subsection(s) of an image, the processing parameter values for the first and second subsections of interest being different; and
a data processor selectively processing, for each subsection of interest at the next position, data acquired by the one or more sensors at the next position in the subsection of interest, in accordance with the one or more already determined processing parameter values for the subsection of interest.

2. A rail vehicle, comprising:
at least one sensor embedded in the rail vehicle and acquiring, at each acquisition instant of each sensor, data corresponding to an acquisition zone of the sensor; and
an electronic module according to claim 1 for processing data acquired by said at least one sensor.

3. A method comprising:
storing, for each of one or more sensors embedded in a rail vehicle, each sensor acquiring data in a respective acquisition zone, and for each of a plurality of positions of the rail vehicle, first and second subsections of interest in the acquisition zone of the sensor, wherein the union of the subsections of interest is strictly less than the acquisition zone and wherein one of the sensors comprises an image sensor capturing images;
determining a next position of the rail vehicle among the plurality of positions;
setting in advance, for the next position, either
(i) a respective value of an image capture parameter for the respective first and second subsections of interest in the respective acquisition zones of the one or more sensors, wherein at least one the image capture parameter is a focal distance, a focal area, a contrast, a white balance, an orientation, a scanning zone, a range, a frequency or frequencies used, or an estimated size of an object sought in a captured images, the image capture parameter values for the first and second subsections of interest being different, and
(ii) at least one value of a values of a processing parameter for the first and second subsections of interest for the determined next position, the processing parameters parameter defining one or more processing operations to be performed on images captured by the sensors, the processing operations comprising, over an entire image or selectively over subsections of an image: detecting presence of objects, identifying types of objects detected, or evaluating distance to a detected object, the processing parameters defining which subsection(s) of an images is/are affected by a processing operation to be applied, or which respective processing operation(s) to apply on each of the subsection(s) of an image, the processing parameter values for the first and second subsections of interest being different; and
selectively processing, for each subsection of interest at the next position, data captured by the one or more sensors in the subsection of interest, in accordance with the one or more already determined processing parameter values for the subsection of interest.

4. The method according to claim 3, wherein said setting in advance is performed as a function of the subsection of interest and to the exclusion of portions of the acquisition zone outside of the subsection of interest.

5. The method according to claim 3, wherein a subsection of interest is comprised within an upcoming trajectory portion and an element to be excluded.

6. The method according to claim 3, wherein a subsection of interest corresponds to one end of a tunnel.

7. The method according to claim 3, wherein said setting in advance is performed as a function of meteorological data.

8. The method according to claim 3, further comprising:
identifying an exploitation problem, or incompleteness, of data acquired by one or more of the sensors; and
triggering provision of complementary data by a data acquisition system not embedded in the rail vehicle.

9. A computer program comprising software instructions which, when executed by a computer, carry out a method according to claim 3.

* * * * *